(12) United States Patent
Sakaguchi et al.

(10) Patent No.: US 10,039,595 B2
(45) Date of Patent: Aug. 7, 2018

(54) MEDICAL MANIPULATOR

(71) Applicant: Karl Storz SE & Co. KG, Tuttlingen (DE)

(72) Inventors: Yuuki Sakaguchi, Fujinomiya (JP); Shinji Ishida, Fujinomiya (JP)

(73) Assignee: Karl Storz SE & Co. KG, Tuttlingen (DE)

( * ) Notice: Subject to any disclaimer, the term of this patent is extended or adjusted under 35 U.S.C. 154(b) by 353 days.

(21) Appl. No.: 14/872,602

(22) Filed: Oct. 1, 2015

(65) Prior Publication Data

US 2016/0022355 A1 Jan. 28, 2016

Related U.S. Application Data

(63) Continuation of application No. PCT/JP2013/060051, filed on Apr. 2, 2013.

(51) Int. Cl.
*A61B 17/29* (2006.01)
*A61B 18/14* (2006.01)
(Continued)

(52) U.S. Cl.
CPC .......... *A61B 18/1445* (2013.01); *A61B 17/29* (2013.01); *A61B 34/70* (2016.02);
(Continued)

(58) Field of Classification Search
CPC ............... A61B 17/29; A61B 18/1445; A61B 2017/00199; A61B 2017/003; A61B 2017/00314; A61B 2017/00398; A61B 2017/0046; A61B 2017/00477; A61B 2017/2903; A61B 2017/2927; A61B 34/70

See application file for complete search history.

(56) References Cited

U.S. PATENT DOCUMENTS 5,254,117 A * 10/1993 Rigby ................ A61B 18/1482
 606/42
5,480,409 A * 1/1996 Riza .................... A61B 17/2909
 606/205

(Continued)

FOREIGN PATENT DOCUMENTS

JP 63234860 A 9/1988
JP 2003208928 A 7/2003
(Continued)

OTHER PUBLICATIONS

International Search Report Application No. PCT/JP2013/060051 Completed: Jul. 1, 2013; dated Jul. 9, 2013 2 pages.
(Continued)

*Primary Examiner* — Michael Peffley
(74) *Attorney, Agent, or Firm* — Whitmyer IP Group LLC

(57) ABSTRACT

A slip ring mechanism for a medical manipulator, the slip ring mechanism including: a rotating rod that rotates together with a drive shaft; rotating terminals that are positioned so as to be coaxial to the rotating rod; conductive members that contact the rotating terminals and are electrically connected to an end effector; holding members that hold the conductive members such that the conductive members are sandwiched between the holding members and the rotating terminals; and contact terminals that contact the rotating terminals so as to be capable of rotating and sliding relative thereto.

13 Claims, 11 Drawing Sheets

(51) Int. Cl.
*A61B 34/00* (2016.01)
*A61B 17/00* (2006.01)
*A61B 18/00* (2006.01)

(52) U.S. Cl.
CPC . *A61B 2017/003* (2013.01); *A61B 2017/0046* (2013.01); *A61B 2017/00199* (2013.01); *A61B 2017/00314* (2013.01); *A61B 2017/00398* (2013.01); *A61B 2017/00477* (2013.01); *A61B 2017/2903* (2013.01); *A61B 2017/2927* (2013.01); *A61B 2018/00178* (2013.01)

(56) References Cited

U.S. PATENT DOCUMENTS

| | | | |
|---|---|---|---|
| 5,716,354 A * | 2/1998 | Hluchy | A61B 18/1442 606/46 |
| 7,632,270 B2 * | 12/2009 | Livneh | A61B 17/29 606/205 |
| 2011/0196286 A1 | 8/2011 | Robertson et al. | |

FOREIGN PATENT DOCUMENTS

| | | | |
|---|---|---|---|
| JP | 2011072570 A | 4/2011 | |
| JP | 2012070857 A | 4/2012 | |
| WO | 9724072 A1 | 7/1997 | |
| WO | 2011100316 A1 | 8/2011 | |

OTHER PUBLICATIONS

European Search Report Application No. EP 13 88 0787 completed: Jul. 20, 2016; dated Jul. 28, 2016 6 pages.

* cited by examiner

MEDICAL MANIPULATOR

FIELD OF THE INVENTION

The present invention relates to a medical manipulator equipped with a slip ring mechanism.

BACKGROUND OF THE INVENTION

In a surgical treatment, without performing a laparotomy or a thoracotomy, small holes are opened in the patient and a forceps or scissors or the like are inserted therein, and surgery in which a desired treatment (so-called endoscopic surgery) is applied to diseased biological tissue or the like in the body is performed. Recently, in these types of procedures, apart from forceps or scissors, a medical manipulator in which operations can be performed in the body with a higher degree of freedom is used.

For example, in Japanese Laid-Open Patent Publication No. 2011-072570, a medical manipulator, which is constituted as an electrosurgical scalpel, is disclosed. In such a medical manipulator, a gripper, which is capable of gripping and engaging an object to be treated, and which can be operated to be opened and closed and to change the posture thereof with respect to the shaft, is disposed on a distal end of a shaft that extends from a handle. In a surgical procedure in which the medical manipulator is used, a distal end working unit including the gripper is inserted into the body cavity, and biological tissue is gripped by the gripper and electrical current is applied thereto, whereby the biological tissue is cauterized.

Among attitude changing operations of the gripper, there are a rolling operation for rotating the gripper about a longitudinal axis thereof, and a tilting action which operates to swing the gripper with respect to the shaft. In the medical manipulator, which is equipped with a gripper in which the rolling operation is possible, for supplying an electrical current to the gripper, for example, a slip ring mechanism can be adopted.

SUMMARY OF THE INVENTION

Generally, with a slip ring mechanism, for enabling electrical conduction between a rotating portion and a non-rotating portion thereof, the rotating portion is equipped with a ring-shaped rotating terminal, and the non-rotating portion is equipped with a contact terminal, which is held in contact with the rotating terminal. In the case it is considered to adopt a slip ring mechanism in the medical manipulator, a member that makes up a conductive path between a gripper and the rotating terminal must be connected to the rotating terminal in a state capable of electrical conduction therewith.

However, in the event that a bonding means such as soldering, an adhesive, or the like, for example, is used for connecting the rotating terminal and the member that constitutes the conductive path, the operation to assemble the slip ring mechanism is made complex. Further, after the medical manipulator has been used to perform a surgical operation, depending on the type of sterilization process that is applied to the medical manipulator, the bonding strength by soldering or the adhesive decreases, and there is a possibility that the electrically conductive state cannot be maintained.

The present invention has been devised while taking into consideration the aforementioned problems, and has the object of providing a medical manipulator for which assembly thereof is easy, and which is equipped with a slip ring mechanism capable of maintaining a suitable electrically conductive state.

For achieving the aforementioned object, a medical manipulator according to the present invention includes an end effector that is capable of carrying out a rolling operation, a drive shaft that transmits at least a rotary driving force to the end effector, and a slip ring mechanism that is connected to the drive shaft. The slip ring mechanism includes a rotating axial body that rotates together with the drive shaft, a rotating terminal arranged coaxially with the rotating axial body, a conductive member that contacts the rotating terminal and is electrically connected to the end effector, a retaining member that holds the conductive member such that the conductive member is sandwiched between the retaining member and the rotating terminal, and a contact terminal that contacts the rotating terminal in a condition enabling rotation and sliding relative to the rotating terminal.

According to the above configuration, for retaining the conductive member in a state of being sandwiched and pressed by the rotating terminal and the retaining member, the slip ring mechanism can easily be assembled without using a bonding means such as soldering, an adhesive, or the like. Further, due to such a structure, even in the case that a sterilization treatment is applied to the medical manipulator including the slip ring mechanism, the electrically conductive state between the conductive member and the rotating terminal can suitably be maintained.

In the above-described medical manipulator, a bent end portion may be disposed on the conductive member, a flange may be disposed on the retaining member, and the bent end portion of the conductive member may be sandwiched between an end surface of the rotating terminal and the flange. According to this configuration, since the bent end portion of the conductive member is retained in a state of being sandwiched in an axial direction between the end surface of the rotating terminal and the flange, the electrically conductive state between the conductive member and the rotating terminal can suitably be assured.

In the above-described medical manipulator, the slip ring mechanism may include a pressure applying member that applies a load in the axial direction to the rotating terminal, the conductive member, and the retaining member. With this configuration, the electrically conductive state between the conductive member and the rotating terminal can suitably be assured.

In the above-described medical manipulator, the pressure applying member may be fixed by screw-engagement to the rotating axial body. According to this configuration, with a simple structure, the conductive member can be effectively maintained while being sandwiched and pressed between the rotating terminal and the retaining member.

In the above-described medical manipulator, the rotating axial body may be displaceable in the axial direction together with the drive shaft, and the slip ring mechanism may include a terminal holder that retains the contact terminal, wherein the terminal holder is rotatable relative to the rotating axial body, and is displaceable in the axial direction in unison with the rotating axial body. According to this configuration, since the terminal holder that retains the contact terminal also is displaced together therewith accompanying displacement of the rotating axial body in the axial direction, when the rotating terminal is displaced in the axial direction, the positional relationship in the axial direction between the rotating terminal and the contact terminal does not change. Consequently, together with displacement of the rotating terminal in the axial direction, the contact terminal does not become caught on the rotating terminal.

In the above-described medical manipulator, in the slip ring mechanism, a first ring unit and a second ring unit, in each of which the rotating terminal, the conductive member, and the retaining member are included, may be arranged along an axial direction of the rotating axial body, and two contact terminals may be provided corresponding respectively to the first ring unit and the second ring unit. According to this structure, a medical manipulator that functions as a bipolar type of electrosurgical scalpel can suitably be handled.

In the above-described medical manipulator, in the slip ring mechanism, a first ring unit and a second ring unit, in each of which the rotating terminal, the conductive member, and the retaining member are included, may be arranged along an axial direction of the rotating axial body, two contact terminals may be provided corresponding respectively to the first ring unit and the second ring unit, and the terminal holder may include a case in which the first ring unit and the second ring unit are accommodated in common, and a retaining member that retains the two contact terminals. According to this configuration, since the first ring unit and the second ring unit are accommodated in a single case, the structure can be simplified.

DETAILED DESCRIPTION OF THE INVENTION

Hereinafter, a preferred embodiment of a medical manipulator according to the present invention will be described in detail below with reference to the accompanying drawings.

Figure 1:
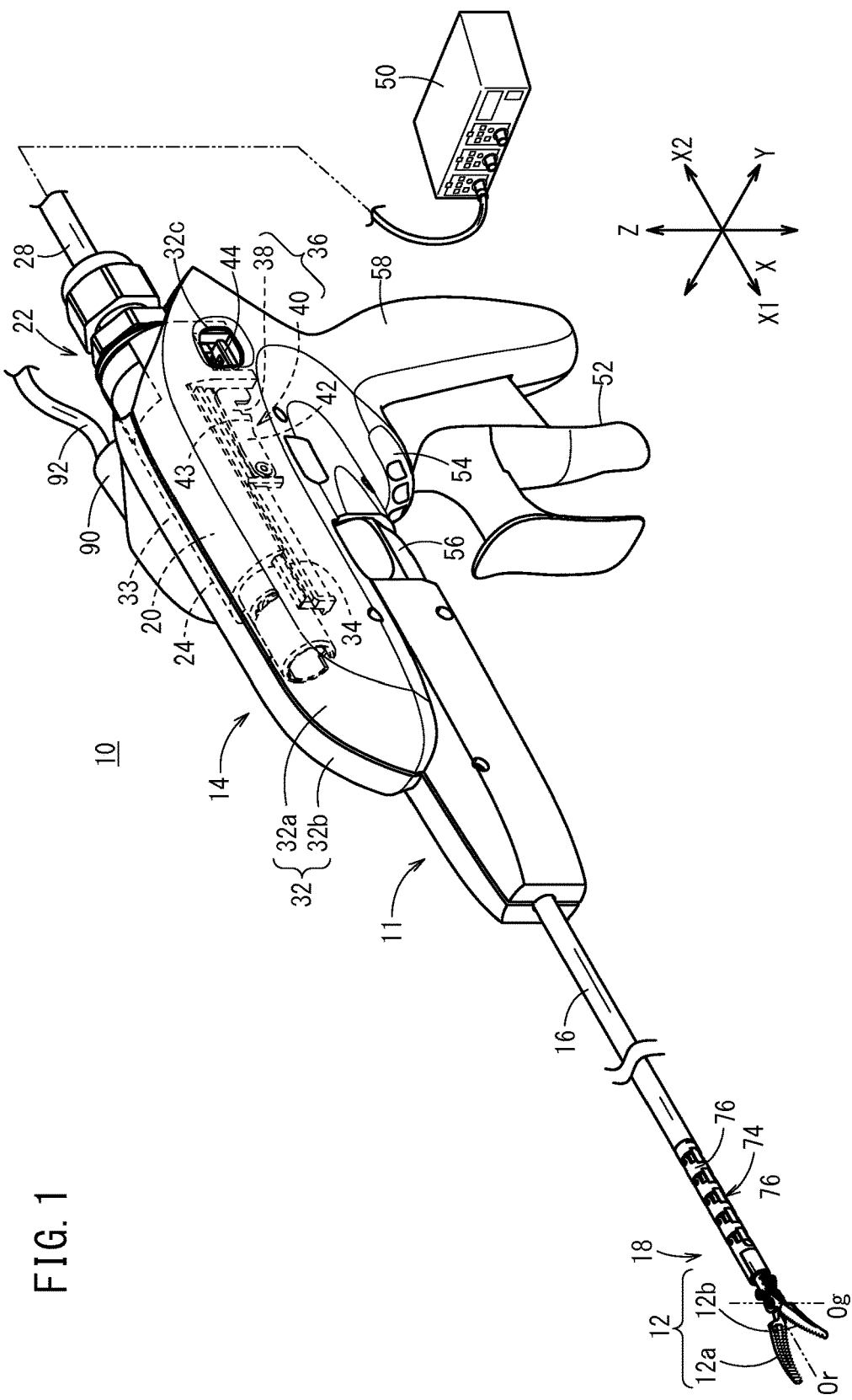
FIG. 1 is a perspective view with partial omission of a medical manipulator according to an embodiment of the present invention.

FIG. 1 is a perspective view with partial omission of a medical manipulator 10 (hereinafter referred to in abbreviated form as a "manipulator 10") according to an embodiment of the present invention. In the following description, in relation to the manipulator 10 and the constituent elements thereof, in the drawings, the X direction indicates a forward and rearward longitudinal direction, the Y direction indicates a left and right lateral direction, and the Z direction indicates an up and down vertical direction. In particular, the X1 direction is a forward direction, and the X2 direction is a rearward direction.

The manipulator 10 is a medical device that grasps a part of the living body or touches the living body using a gripper 12 (end effector) provided at the distal end thereof, and carries out a predetermined treatment. With the present embodiment, the manipulator 10 functions as an electrosurgical scalpel that carries out a predetermined treatment (e.g., cauterization, etc., by heat) by supplying an electrical current to a biological tissue that serves as a treatment object. As biological tissues suitable as treatment objects, there may be cited, for example, tumors (lesions), muscles, blood vessels, or nerves, and the like.

The manipulator 10 comprises a handle 14, a connecting shaft 16 that extends from the handle 14, a distal end working unit 18 disposed on a distal end of the connecting shaft 16 including the gripper 12, and a drive unit 22 that is capable of attachment and detachment to and from the handle 14. A manipulator main body 11 is made up from the handle 14, the connecting shaft 16, and the distal end working unit 18.

With the manipulator 10 according to the present embodiment, a motor 20 (driving source), which implements a predetermined operation on the distal end working unit 18, is disposed not in the manipulator main body 11, but in the drive unit 22. In a state in which the drive unit 22 has been taken out from the manipulator main body 11, the driving force from the motor 20, which is mounted in the drive unit 22, is not transmitted to the distal end working unit 18. On the other hand, in a state in which the drive unit 22 is mounted on the handle 14, when the motor 20 is driven, the driving force of the motor 20 is transmitted to the distal end working unit 18.

The drive unit 22 includes a housing 24, the motor 20 (drive source) disposed inside the housing 24, and a drive coupling 26 (drive member) that is fixed to an output shaft 21 of the motor 20. A cable 28 including power lines and signal lines is connected to the proximal end side of the drive unit 22.

Figure 3:
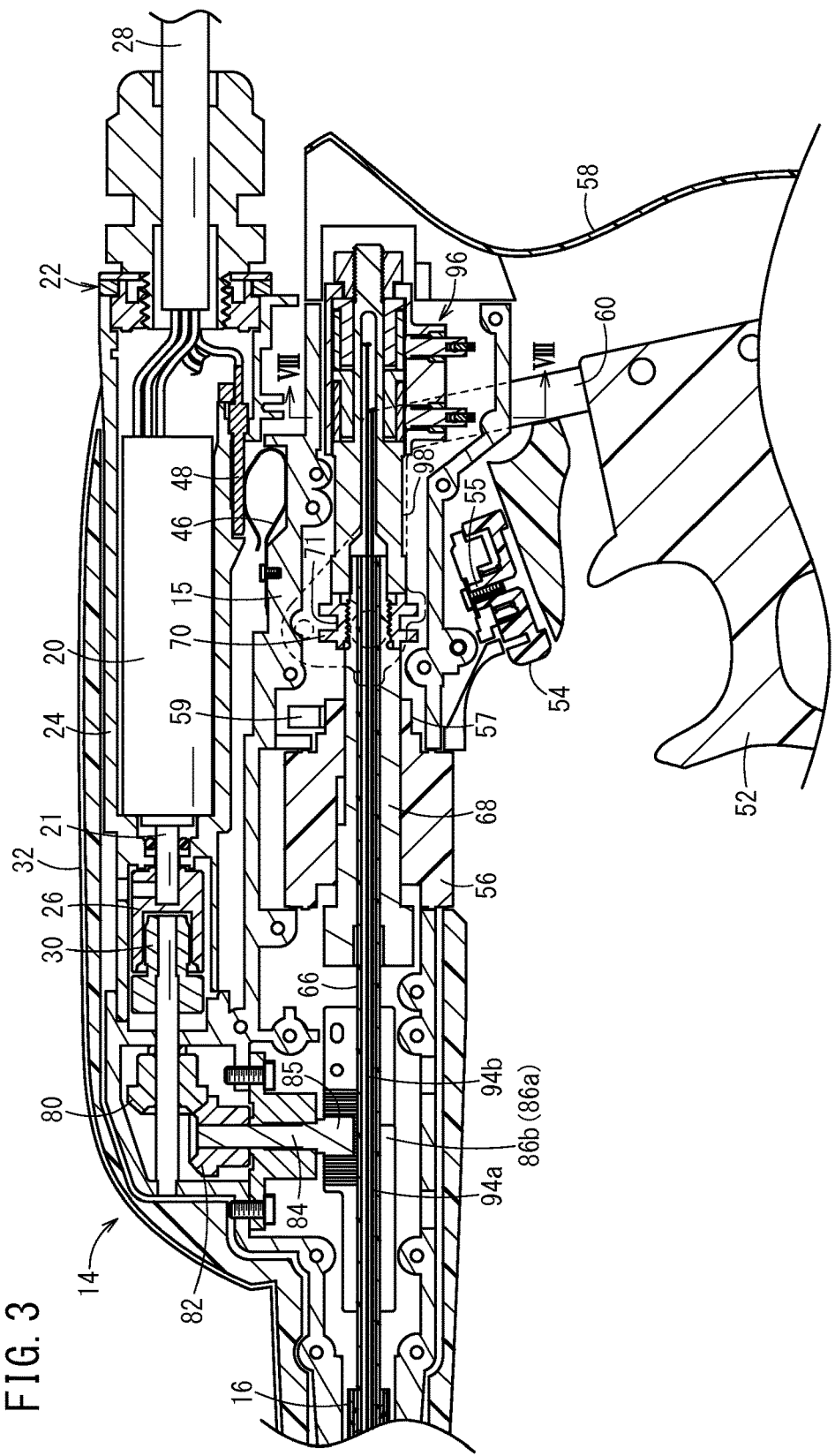
FIG. 3 is a vertical cross-sectional view with partial omission of a handle of the medical manipulator illustrated in FIG. 1.

FIG. 3 is a vertical cross-sectional view with partial omission of the handle 14. As shown in FIG. 3, in a state in which the drive unit 22 is attached to the handle 14, the drive coupling 26, which is fixed to the output shaft 21 of the motor 20, is fitted (enmeshed) with a driven coupling 30 (driven member) disposed on the side of the handle 14. In the state with the drive coupling 26 and the driven coupling 30 fitted together, when the motor 20 is driven, the rotary driving force of the motor 20 is transmitted to the side of the handle 14 through the drive coupling 26 and the driven coupling 30.

In the handle 14, guide rails (not shown) that extend along a longitudinal (forward and rearward) direction of the handle 14, are provided on both left and right sides on an inside surface of a casing 32. As shown in FIG. 1, groove-shaped guide receiving members 34 that extend in the longitudinal direction of the drive unit 22 are disposed on side surfaces on both left and right sides of the housing 24.

When the drive unit 22 is attached with respect to the handle 14, under a guiding action of the guide rails and the guide receiving members 34, the drive unit 22 can be moved smoothly relative to the handle 14. Consequently, the drive unit 22 can be mounted easily and reliably at an accurate positional relationship with respect to the handle 14. Even without providing the guide rails and the guide receiving members 34, a configuration may be provided in which a similar guiding action to that described above is obtained, by inner wall surfaces in the interior of the handle 14 constituting a mounting hole 33, and outer wall surfaces of the housing 24 of the drive unit 22.

As shown in FIG. 1, in the drive unit 22, a lock mechanism 36 is provided that restricts the drive unit 22 so as not to become detached from the handle 14, in a state in which the drive unit 22 has been attached to the handle 14. The lock mechanism 36 includes an engagement member 38 disposed on the handle 14, and a lever device 40 disposed on the drive unit 22.

The lever device 40 includes a lever member 42, an operating tab 44, and a lever biasing member (not shown). The lever member 42 is swingable with respect to the housing 24, and is equipped with an engagement pawl 43. The operating tab 44 is disposed on a proximal end of the lever member 42. The lever biasing member biases the lever member 42 elastically in a direction in which the engagement pawl 43 projects (a downward direction as shown in the illustrated example).

When the drive unit 22 is attached to the handle 14, the engagement pawl 43 disposed on the lever member 42 engages with the engagement member 38 provided inside the handle 14, whereby the drive unit 22 is prevented from becoming detached and separating away from the handle 14. On the other hand, by releasing the engagement between the engagement member 38 and the engagement pawl 43 of the lever member 42, the drive unit 22 is capable of being detached from the handle 14.

On an upper end side of the handle 14, the mounting hole 33 is provided, which opens rearwardly. The drive unit 22 is inserted into the mounting hole 33, and thus can be mounted with respect to the handle 14. More specifically, the drive unit 22 is capable of being attached to and detached from the proximal end side of the handle 14. In a state in which the drive unit 22 is mounted in the handle 14, so that operating tabs 44, which are disposed on the drive unit 22, can be touched and operated by the user, the operating tabs 44 are exposed through openings 32c provided on side surfaces on left and right sides of the handle 14.

As shown in FIG. 3, handle side terminal members 46 are disposed on the handle 14, and unit-side terminal members 48 are disposed on the drive unit 22. The handle side terminal members 46 and the unit side terminal members 48, respectively, are disposed with a plurality of such members each. In a state in which the drive unit 22 is attached to the handle 14, the handle-side terminal members 46 and the unit-side terminal members 48 provided on the drive unit 22 are placed in contact. According to this structure, the operating state of a tilting switch 54 can be detected by a controller 50, and the controller 50 can appropriately control driving of the motor 20.

The form of use can be one in which, concerning the manipulator 10 that is constructed in the foregoing manner, the manipulator main body 11 can be discarded after being used a predetermined number of times, whereas the drive unit 22 can be used repeatedly many times by changing the manipulator main body 11 that is connected with the drive unit 22.

As shown in FIG. 1, the drive unit 22 of the manipulator 10 is used in a condition of being connected to the controller 50 through the cable 28. The controller 50 controls the supply of power and driving of the motor 20, and receives electrical power from an external power source.

Figure 2:
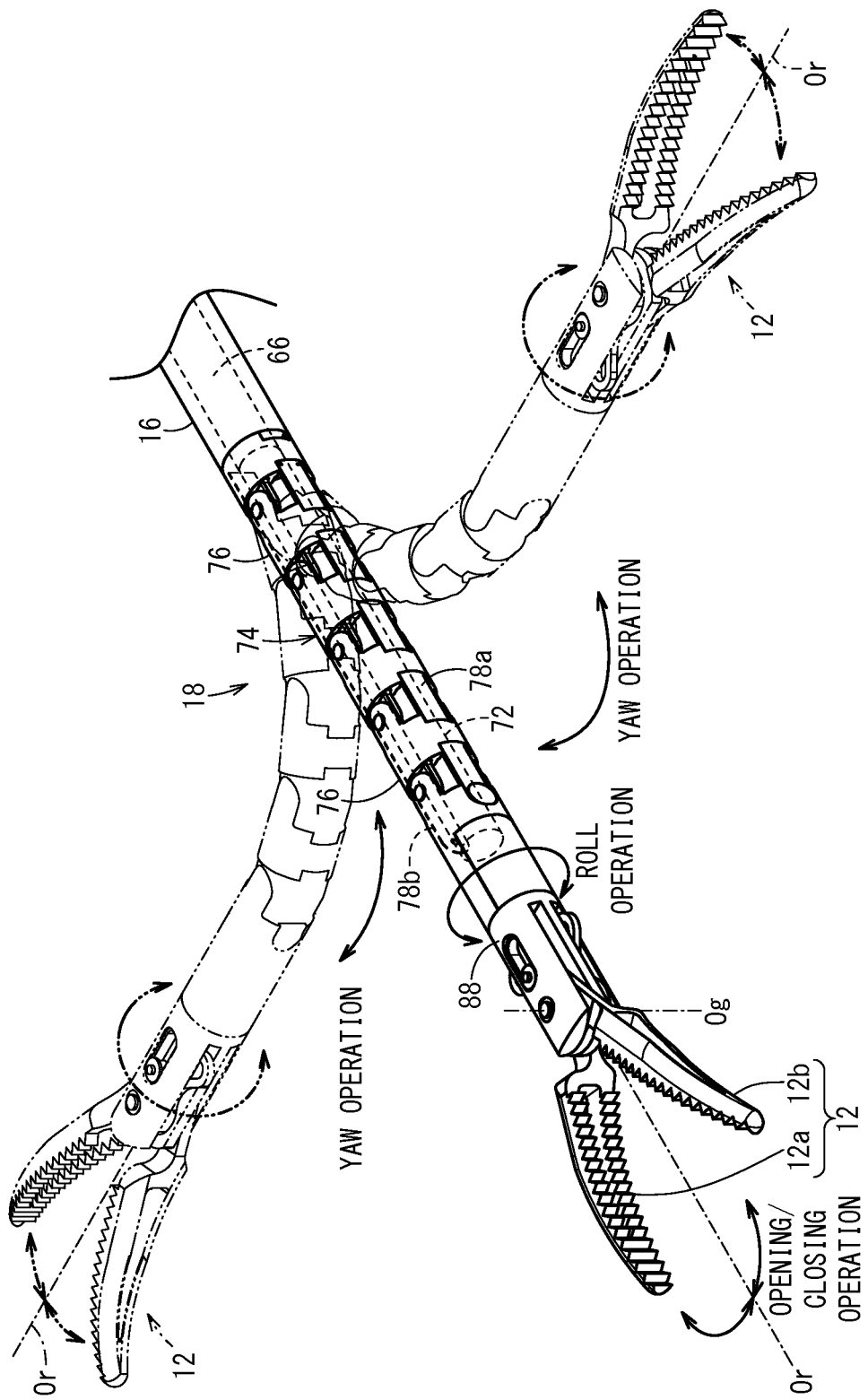
FIG. 2 is a perspective view of a distal end working unit of the medical manipulator illustrated in FIG. 1.

Next, the structure of the manipulator main body 11 will be described in greater detail. As shown in FIG. 2, the gripper 12 is capable of making opening and closing movements, and serves as a portion for gripping biological tissue, and cauterizing the biological tissue by conduction of current through the tissue. The gripper 12 of the present illustrated example includes a first gripper member 12a and a second gripper member 12b, which are capable of swinging or pivoting in mutually opposite directions about a gripper axis Og. Among the gripper members, one of the gripping members may be constituted as a fixed member, whereas the other may be constituted as a movable member.

The posture of the distal end working unit 18 including the gripper 12 can be changed at a plurality of degrees of freedom with respect to the connecting shaft 16. In the present embodiment, the distal end working unit 18 can carry out a "tilting operation" (swinging operation) in which the distal end working unit 18 is operated to tilt or warp in left and right directions (Y directions) with respect to an axis of the connecting shaft 16, and a "rolling operation" in which the distal end working unit 18 is rotated about the axial line of the connecting shaft 16 (roll axis Or) in the longitudinal direction of the distal end working unit 18. In the present embodiment, the tilting operation of the distal end working unit 18 is a yaw operation carried out by swinging in right and left directions. However, instead of such a yaw operation, the tilting operation may be a pitch operation carried out by swinging in a vertical direction.

The connecting shaft 16 is an oblong small diameter tubular member that connects the handle 14 and the distal end working unit 18. In FIG. 1, a portion of the connecting shaft 16 is omitted from illustration, and the connecting shaft is rendered shorter than it actually is. A plurality of members configured to make up a power transmission mechanism are inserted through and arranged in a hollow portion of the connecting shaft 16. Such a power transmission mechanism transmits, from the handle 14 to the distal end working unit 18, power that is necessary for carrying out the opening and closing operation of the gripper 12, and the rolling operation and the tilting operation of the distal end working unit 18.

A structure may be provided in which one or a plurality of joints are provided at an intermediate location in the longitudinal direction of the connecting shaft 16 to enable a tilting operation by the joints. Further, a structure may be provided in which the rolling operation is enabled at the proximal end of the connecting shaft 16, or at an intermediate location in the longitudinal direction of the connecting shaft 16.

The handle 14 is a portion that is gripped by an operator during use of the manipulator 10, and by input operating members (in the present embodiment, a later described lever 52, the tilting switch 54, and a rotating knob 56) being touched and operated by a finger, drives the distal end working unit 18 that is connected to the distal end of the connecting shaft 16.

According to the present embodiment, the handle 14 is configured in the form of a pistol to facilitate gripping thereof by a user with one hand. The handle 14 includes the casing 32 made up from a left-side cover 32a and a right-side cover 32b. A handle frame 15 (see FIGS. 3 and 8) and drive components, etc., are arranged in the interior of the casing 32. The lever 52 constituting an opening and closing operating unit, the tilting switch 54 constituting a tilt operating unit, and the rotating knob 56 constituting a rolling operating unit are disposed on the handle 14.

The opening and closing operation of the gripper 12 is carried out by mechanically transmitting the operation of the lever 52, which is provided on the handle 14, to the distal end working unit 18. More specifically, in the present illustrated example, the lever 52 is constructed as a manual operating member, and opening and closing operations of the gripper 12 are performed not by a motor drive, but by a manual drive on the basis of an operating force from the operator.

The lever 52 is disposed so as to be displaceable in forward and rearward directions with respect to a grip 58. As shown in FIG. 3, in the interior of the grip 58, a lever arm 60 is fixed to the lever 52. On an upper end part of the lever arm 60, a handle frame 15 is connected in a swingable manner.

On the other hand, in the interior of the handle 14, a hollow drive shaft 66 that extends in the longitudinal direction of the handle 14 is supported rotatably. A slide shaft 68, which is capable of movement together with the drive shaft 66 in the axial direction as well as being rotatable, is fixed to an outer side of the drive shaft 66. An engagement ring 70 having an annular groove 71 therein is fixed to a portion near the proximal end of the slide shaft 68. A protrusion (not shown) provided on the lever arm 60 is inserted into the annular groove 71 of the engagement ring 70.

A distal end side part of the drive shaft 66 is arranged for insertion through the interior of the connecting shaft 16. As shown in FIG. 2, a flexible hollow tube 72 is fixed to a distal end part of the drive shaft 66. The hollow tube 72 is inserted rotatably and movably in the axial direction through the interior of a bending portion 74 that is connected to the distal end of the connecting shaft 16.

When the lever 52 is pressed out forwardly with respect to the grip 58, by an engagement action between the engagement ring 70 and the protrusion provided on the lever arm 60, the engagement ring 70 is displaced in a forward direction. Accompanying such forward displacement of the engagement ring 70, the slide shaft 68, the drive shaft 66, and the hollow tube 72 also are displaced in the forward direction. At the distal end working unit 18, movement of the hollow tube 72 at this time is converted, thereby opening the gripper 12.

Conversely, when the lever 52 is pulled in rearwardly with respect to the grip 58, by an engagement action between the engagement ring 70 and the protrusion provided on the lever arm 60, the engagement ring 70 is displaced in a rearward direction. Accompanying such rearward displacement of the engagement ring 70, the slide shaft 68, the drive shaft 66, and the hollow tube 72 also are displaced in the rearward direction. At the distal end working unit 18, movement of the hollow tube 72 at this time is converted, thereby closing the gripper 12.

A structure may also be adopted in which the opening and closing operation of the gripper 12 is performed by a motor drive.

The distal end working unit 18 is capable of being tilted laterally (yaw operation) by the bending portion 74 connected to a distal end of the connecting shaft 16. As shown in FIG. 2, the bending portion 74 has a plurality of joint members 76, which are coupled rotatably within a predetermined angular range to one another. A pair of drive belts 78a, 78b is inserted through the plurality of joint members 76, on left and right side portions in the bending portion 74. Although in a state in which the joint members 76 are aligned coaxially, the bending portion 74 exhibits a linear shape, when the adjacent joint members 76 themselves are mutually tilted, the bending portion 74 exhibits a curved shape as a whole.

The tilting operation of the distal end working unit 18 is carried out by a driving force of the motor 20, which is controlled responsive to the operating state of the tilting switch 54 shown in FIG. 1 being mechanically transmitted to the distal end working unit 18. In the present embodiment, the tilting switch 54 is disposed so as to be capable of rotating within a predetermined angular range about a switch shaft 55. When the tilting switch 54 is operated to rotate in a clockwise direction as viewed in plan, the distal end working unit 18 is tilted in a rightward direction. When the tilting switch 54 is operated to rotate in a counterclockwise direction as viewed in plan, the distal end working unit 18 is tilted in a leftward direction.

More specifically, when the tilting switch 54 that is disposed on the handle 14 is operated, the controller 50 controls driving of the motor 20 responsive to the operating state thereof. The driving force of the motor 20 is transmitted toward the handle 14 through the drive coupling 26 and the driven coupling 30 that are shown in FIG. 3.

In the handle 14, rotation of the driven coupling 30 is transmitted to a pair of slide members 86a, 86b having rack members through a pair of mutually intermeshed bevel gears 80, 82, and a gear shaft 84 that is connected coaxially with the bevel gear 82. Note that in FIG. 3, only one of the slide members 86b (on the left-hand side) is shown.

The slide members 86a, 86b are capable of sliding forward and rearward in the interior of the handle 14, and are enmeshed with a gear 85, respectively, on left and right sides of the gear 85 disposed on the gear shaft 84. Accompanying rotation of the gear 85, the slide members 86a, 86b are displaced mutually in opposite directions. Movements of the slide members 86a, 86b, which are displaced mutually in opposite directions, are transmitted to the drive belts 78a, 78b of the distal end working unit 18 (see FIG. 2), through a non-illustrated transmission member that is inserted in the connecting shaft 16. Between the pair of drive belts 78a, 78b, one is pulled in the proximal end direction, and the other is pushed in the distal end direction, whereby the bending portion 74 is tilted to the left or to the right.

The distal end working unit 18, at a portion thereof located more toward the distal end side than the bending portion 74, is capable of executing a rolling operation about the roll axis Or. The rolling operation is carried out by mechanically transmitting a drive force to the distal end working unit 18, based on a rotary operation made with respect to the rotating knob 56 provided on the handle 14.

More specifically, in FIG. 3, accompanying rotation of the rotating knob 56, the slide shaft 68 that is arranged on an inner side of the rotating knob 56, and the drive shaft 66 that is fixed to an inner side of the slide shaft 68 are rotated. Although the slide shaft 68 is capable of being moved in an axial direction with respect to the rotating knob 56, relative rotation therebetween is impossible.

The drive shaft 66 is fixed to the slide shaft 68, so that relative movement in the axial direction and relative rotation therebetween is impossible. The drive shaft 66 is supported rotatably in the interior of the handle 14, and a distal end side portion thereof is arranged for insertion through the interior of the connecting shaft 16.

As shown in FIG. 2, the hollow tube 72 is fixed to a distal end part of the drive shaft 66. The hollow tube 72 is constituted as a torque tube, having a flexibility that is capable of following or tracking with bending of the bending portion 74, and which also is capable of rotating in addition to bending in following relation to the bending portion 74.

Together with rotation of the hollow tube 72, a gripper retaining member 88, and the gripper 12 that is retained in the gripper retaining member 88 are rotated about the roll axis Or. More specifically, a rotary driving force based on the rotary operation input to the rotating knob 56 is transmitted to the gripper 12 through the slide shaft 68, the drive shaft 66, the hollow tube 72, and the gripper retaining member 88.

In this manner, the rotary driving force input to the rotating knob 56 is transmitted to the gripper 12 through the slide shaft 68, the drive shaft 66, and the hollow tube 72 that have an unlimited range of angular rotation. Further, lead wires 94a, 94b extend through the hollow tube 72 and the interior of the drive shaft 66, and are rotated integrally with the hollow tube 72 and the drive shaft 66. Thus, with the manipulator 10, the distal end working unit 18 is capable of carrying out the rolling operation continuously without any limitation on the range of angular rotation thereof. Consequently, a change in the posture of the gripper 12 by such a rolling operation can be carried out any number of times. Although omitted from illustration in FIG. 3, a plurality of latch teeth 57 that project radially outward are provided at intervals in the circumferential direction on the rotating knob 56 (in the illustrated example, on a proximal end portion of the rotating knob 56). A latch piece 59 of a plate spring that is provided in the interior of the handle 14 abuts against the latch teeth 57. When the rotating knob 56 is rotated, concave/convex shapes formed by the plurality of latch teeth 57 are moved relatively with respect to the latch piece 59. Accordingly, the latch piece 59 is elastically deformed. As a result, an appropriate clicking feeling is obtained, whereby the rotary operation of the rotating knob 56 can be carried out intuitively.

In the present embodiment, the rotating knob 56 is constructed as a manual operating member, and the rolling operation of the distal end working unit 18 is performed not by a motor drive, but by a manual drive on the basis of an operating force from the operator. A structure may also be adopted in which the rolling operation of the distal end working unit 18 is performed by a motor drive.

In the manipulator 10, a power supplying connector 90 can be connected to the handle 14, to enable the manipulator 10 to be used as an electrosurgical scalpel. The power supplying connector 90 is connected to a non-illustrated high frequency power supply device through an energizing cable 92, and by the high frequency power supply device, a high frequency voltage is applied in order to electrically energize the gripper 12.

In FIG. 2, ends of the lead wires 94a, 94b are connected, respectively, through non-illustrated conductive elements at an inner portion of the gripper retaining member 88, to the first gripper member 12a and the second gripper member 12b. The lead wires 94a, 94b are inserted through the interior of the hollow tube 72 and the interior of the drive shaft 66. As shown in FIG. 3, other ends of the respective lead wires 94a, 94b extend in the proximal end direction beyond the proximal end of the drive shaft 66, and are connected to a slip ring mechanism 96 that is disposed in the interior of the handle 14.

Figure 4:
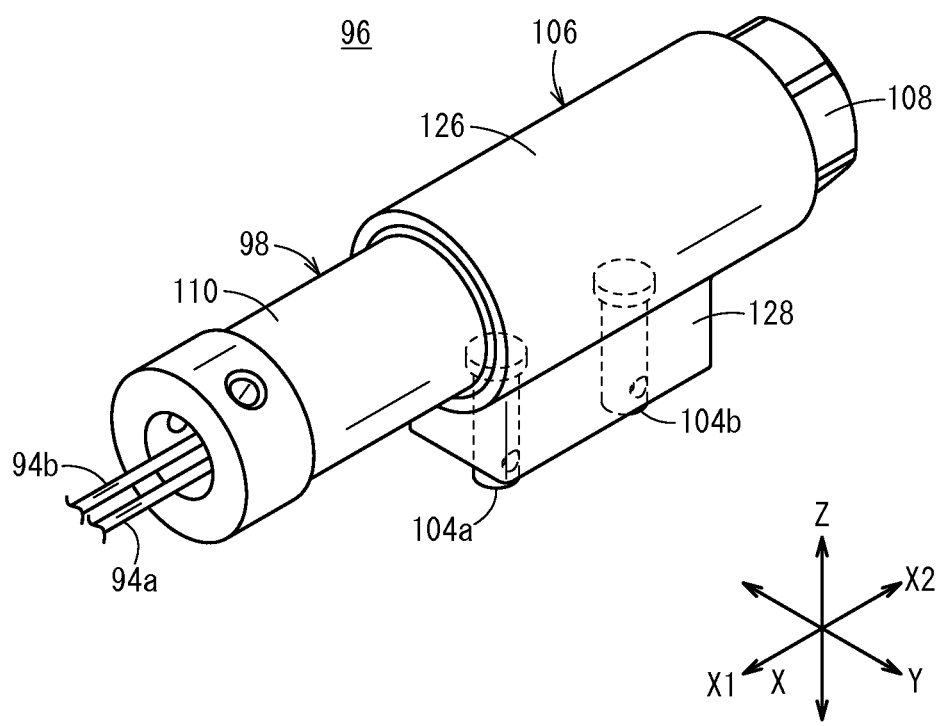
FIG. 4 is a perspective view of a slip ring mechanism provided in the medical manipulator illustrated in FIG. 1.
Figure 5:
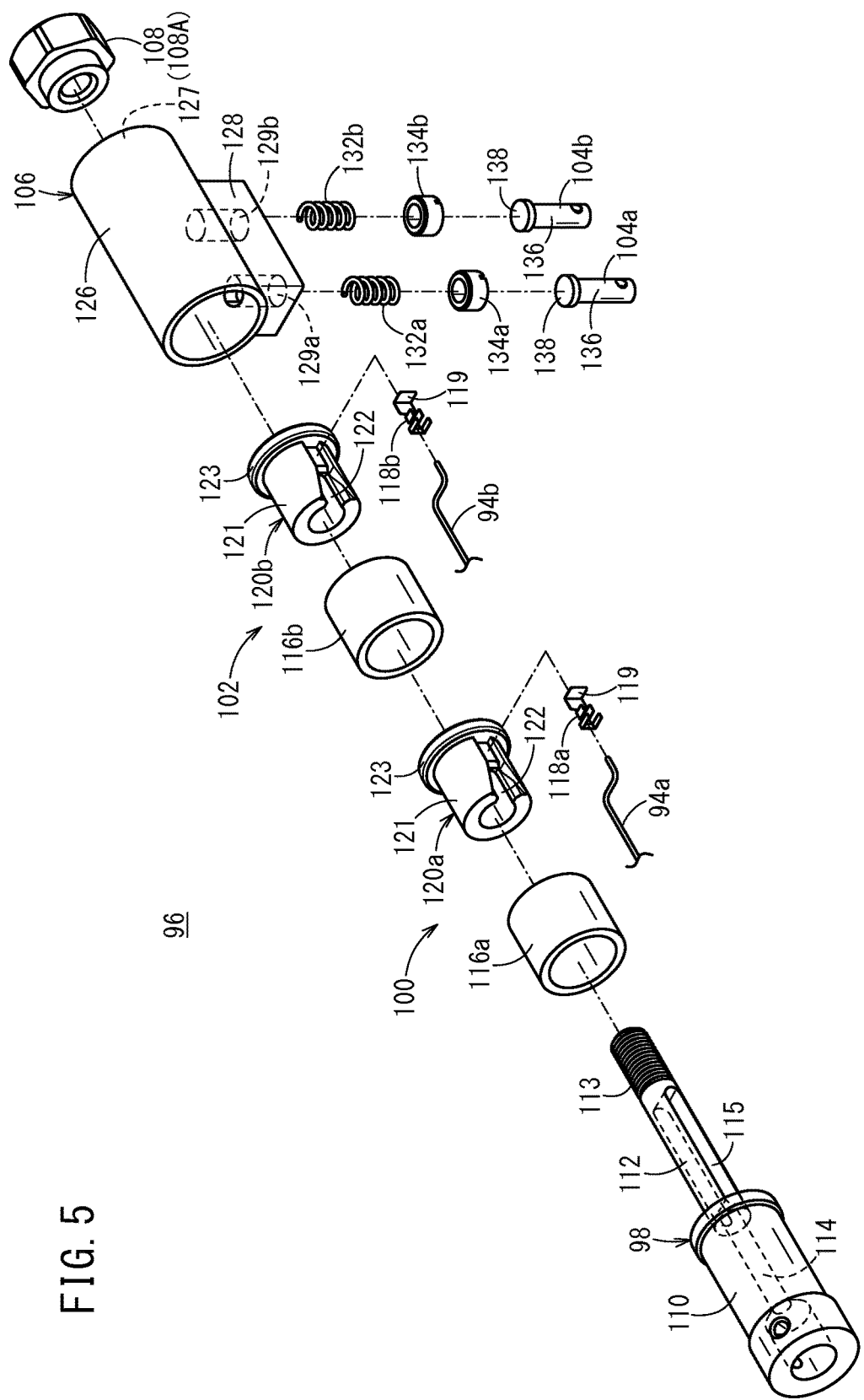
FIG. 5 is an exploded perspective view of the slip ring mechanism shown in FIG. 4.
Figure 6:
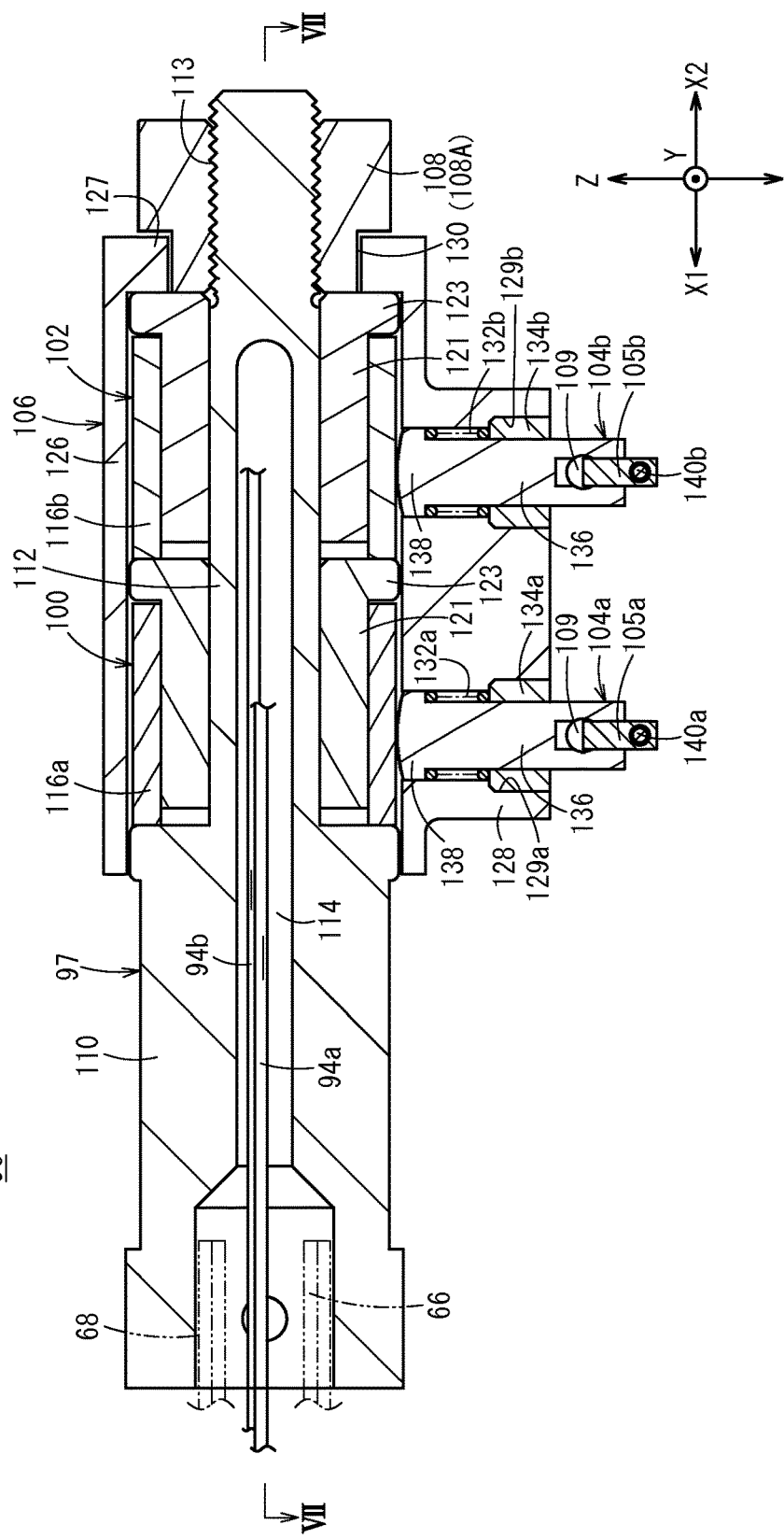
FIG. 6 is a vertical cross-sectional view of the slip ring mechanism shown in FIG. 4.
Figure 7:
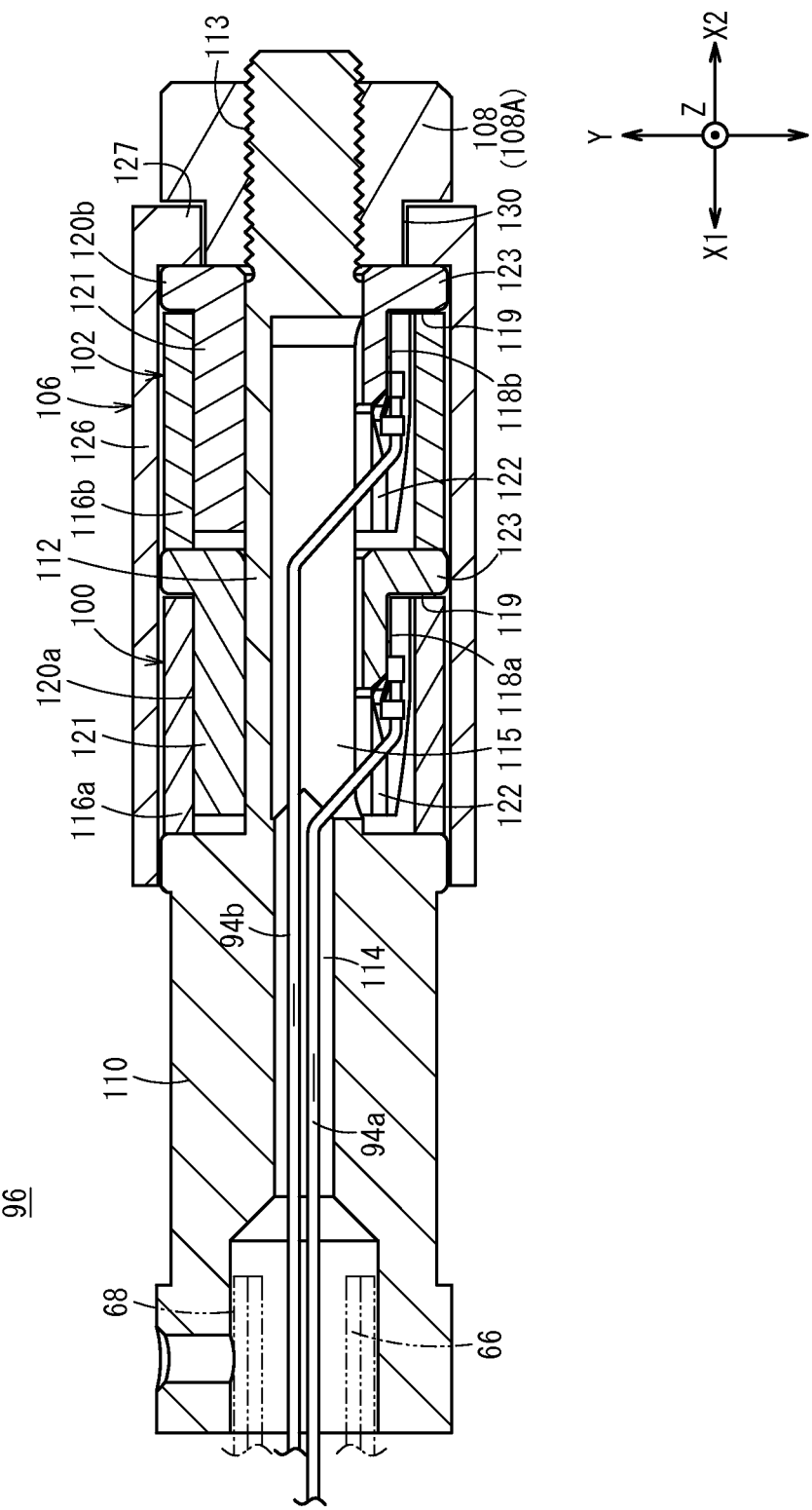
FIG. 7 is a cross-sectional view taken along line VII-VII of FIG. 6.
Figure 8:
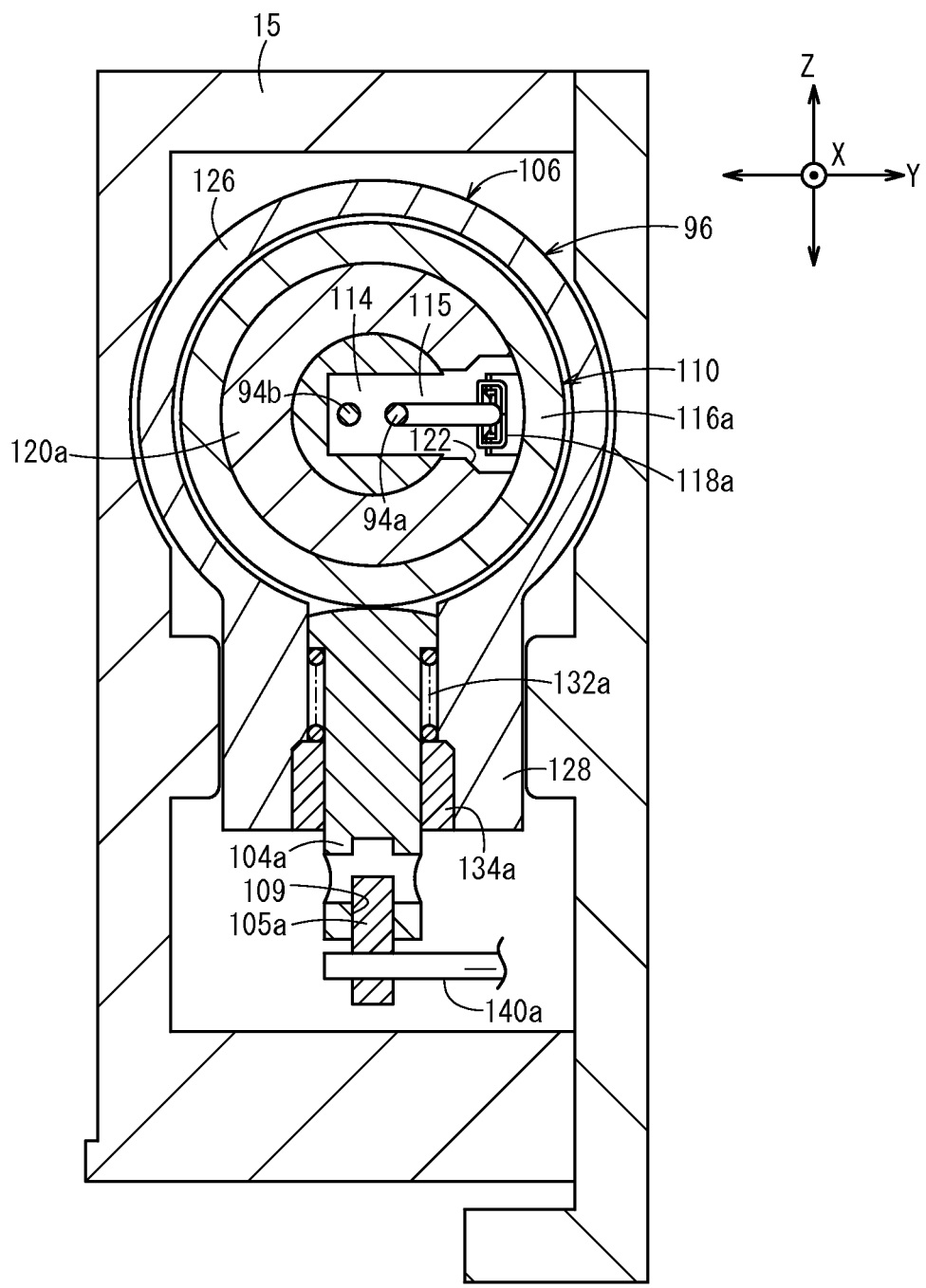
FIG. 8 is a cross-sectional view taken along line VIII-VIII of FIG. 3.

The slip ring mechanism 96 is a mechanism that maintains a conductive path in the interior of the handle 14, and carries out supply of electricity to the gripper 12, even at times that the hollow tube 72 and the drive shaft 66 are rotated. FIG. 4 is a perspective view of the slip ring mechanism 96. FIG. 5 is an exploded perspective view of the slip ring mechanism 96. FIG. 6 is a vertical cross-sectional view of the slip ring mechanism 96. FIG. 7 is a cross-sectional view taken along line VII-VII of FIG. 6. FIG. 8 is a cross-sectional view taken along line VIII-VIII of FIG. 3.

In the present embodiment, the slip ring mechanism 96 includes a rotating axial body 98, a first ring unit 100, a second ring unit 102, two contact terminals 104a, 104b, a terminal holder 106, and a pressure applying member 108.

The rotating axial body 98 rotates together with the drive shaft 66. In the present illustrated example, the rotating axial body 98 is connected and fixed coaxially to the proximal end of the drive shaft 66. A large diameter portion 110 and a support shaft 112, which projects in the direction of the proximal end from the large diameter portion 110, are provided on the rotating axial body 98. Male threads 113 are formed on the proximal end of the support shaft 112.

A wiring hole 114 that extends in an axial direction is disposed in the rotating axial body 98. The wiring hole 114 communicates with an oblong hole-shaped side hole 115 disposed in the support shaft 112. The lead wires 94a, 94b, which project in the direction of the proximal end beyond the drive shaft 66, are connected, through the wiring hole 114 and the side hole 115, to later-described conductive members 118a, 118b.

The first ring unit 100 includes a rotating terminal 116a, the conductive member 118a, and a retaining member 120a. The rotating terminal 116a is of a hollow cylindrical shape, and is arranged coaxially with the rotating axial body 98. The rotating terminal 116a is constituted from an electrically conductive material made of metal or the like. For example, if the rotating terminal 116a is constituted from a material (stainless steel or the like) that is highly resistant to corrosion, then in the case that a sterilization treatment in which steam is used is applied to the manipulator main body 11 including the slip ring mechanism 96, generation of an oxide film on the rotating terminal 116a can suitably be suppressed.

The conductive member 118a is constituted from an electrically conductive material such as metal or the like, which contacts the rotating terminal 116a. More specifically, in the present illustrated example, the conductive member 118a is constituted by a bent plate-shaped body. The lead wire 94a is coupled to and held on an end side of the conductive member 118a. A bent end portion 119 is disposed on another end side of the conductive member 118a.

The retaining member 120a is constituted from an insulating material such as a resin or the like, and is a member that is formed in a hollow cylindrical shape as a whole. The support shaft 112 of the rotating axial body 98 is inserted through an inner side of the retaining member 120a. Within the retaining member 120a, a notch 122 is provided on a tubular portion 121 thereof that is inserted into the inner side of the rotating terminal 116a. The lead wire 94a is passed through the notch 122, and is connected to the conductive member 118a. An annular flange 123, which bulges in a radial outward direction and extends in a circumferential direction therearound, is provided on a proximal end side of the tubular portion 121. The bent end portion 119 of the conductive member 118*a* is sandwiched and gripped between an end surface of the rotating terminal 116*a* and the flange 123 of the retaining member 120*a*.

The second ring unit 102 is constructed in the same manner as the first ring unit 100. More specifically, the second ring unit 102 includes a rotating terminal 116*b*, the conductive member 118*b*, and a retaining member 120*b*, which are constructed in the same manner as the rotating terminal 116*a*, the conductive member 118*a*, and the retaining member 120*a* of the first ring unit 100.

The first ring unit 100 and the second ring unit 102 are arranged adjacently in the axial direction on the support shaft 112 of the rotating axial body 98. Therefore, the flange 123 of the retaining member 120*a* on the first ring unit 100 is in contact with an end surface of the rotating terminal 116*b* on the second ring unit 102.

The pressure applying member 108 is fixed to the rotating axial body 98, and applies a load in the axial direction with respect to the first ring unit 100 and the second ring unit 102. The pressure applying member 108 of the present illustrated example is a nut 108A that is screw-engaged with the male threads 113 disposed on the rotating axial body 98. In a state in which the pressure applying member 108 is attached to the rotating axial body 98 and is fastened thereon, the first ring unit 100 and the second ring unit 102 are sandwiched between the rotating axial body 98 and the nut 108A. Therefore, the conductive member 118*a* on the first ring unit 100 is retained by being sandwiched and pressed between the rotating terminal 116*a* and the retaining member 120*a*, and the conductive member 118*b* on the second ring unit 102 is retained by being sandwiched and pressed between the rotating terminal 116*b* and the retaining member 120*b*.

In the slip ring mechanism 96, the rotating axial body 98, the first ring unit 100, the second ring unit 102, and the pressure applying member 108 are rotated together in unison. Further, the lead wires 94*a*, 94*b* which are coupled to the conductive members 118*a*, 118*b*, also are rotated together integrally with the rotating axial body 98, the first ring unit 100, the second ring unit 102, and the pressure applying member 108. Hereinafter, in the slip ring mechanism 96, the rotating axial body 98, the first ring unit 100, the second ring unit 102, and the pressure applying member 108 will be referred to collectively as a "rotor unit 97".

The two contact terminals 104*a*, 104*b* are constituted from a conductive material such as metal or the like, and are placed in sliding contact with the rotating terminals 116*a*, 116*b* in a state enabling relative rotation with respect to the rotating terminals 116*a*, 116*b*. The respective contact terminals 104*a*, 104*b* of the present illustrated example are pin-shaped, having shaft portions 136, and head portions 138 that are expanded in diameter with respect to the shaft portions 136. The respective head portions 138 are retained in the terminal holder 106, in a state of contact with outer circumferential surfaces of the rotating terminals 116*a*, 116*b*. The terminal holder 106 includes a hollow cylindrical case 126 that covers the first ring unit 100 and the second ring unit 102, and a retaining part 128 that projects out from a portion in the circumferential direction of the case 126.

As shown in FIG. 6, an inwardly projecting portion 127, which projects in a radial inward direction, is disposed on a proximal end of the case 126. The inwardly projecting portion 127 is arranged in the interior of an annular recess 130 that is formed by the pressure applying member 108 and the retaining member 120*b* of the second ring unit 102. Consequently, positioning of the terminal holder 106 in the axial direction with respect to the rotating axial body 98 is effected.

Two retaining holes 129*a*, 129*b* are disposed in the retaining part 128. The contact terminals 104*a*, 104*b* are arranged in a state of being inserted, respectively, in the retaining holes 129*a*, 129*b*. Furthermore, biasing members 132*a*, 132*b* (coil springs in the present illustrated example) and fixing parts 134*a*, 134*b* are arranged in the retaining holes 129*a*, 129*b*.

Respective ends of the biasing members 132*a*, 132*b* abut against the head portions 138 of the contact terminals 104*a*, 104*b*, and other ends thereof abut against the fixing parts 134*a*, 134*b*, and thereby, the biasing members 132*a*, 132*b* are retained in a state of being compressed elastically in the retaining holes 129*a*, 129*b*. The fixing parts 134*a*, 134*b* of the present illustrated example are ring-shaped, and a fixed to the retaining part 128. Moreover, as means for fixing the fixing parts 134*a*, 134*b* with respect to the retaining part 128, for example, screw-fitting, an adhesive, or the like may be employed.

Due to the elastic force of the biasing members 132*a*, 132*b*, the contact terminals 104*a*, 104*b* are pressed respectively against the outer circumferential surfaces of the rotating terminals 116*a*, 116*b*, and are kept in contact at all times with the outer circumferential surfaces thereof. Even if foreign matter becomes adhered to, or an oxide film is formed on surfaces of the rotating terminals 116*a*, 116*b* accompanying rotation of the rotating terminals 116*a*, 116*b*, such foreign matter or the oxide film is scraped off, and the contact points are activated (refreshed). The contact terminals 104*a*, 104*b* are connected on an outer side of the terminal holder 106 to lead wires 140*a*, 140*b* (see FIG. 6) that lead to energizing terminals (terminals connected to the power supplying connector 90 shown in FIG. 1) provided in the handle 14. As shown in FIG. 8, which is a cross-sectional view taken along line VIII-VIII in FIG. 3, the lead wire 140*a* is fixed to the contact terminal 104*a* through a fixing pin 105*a*. The fixing pin 105*a* is inserted and fixed in a hole 109 provided in the contact terminal 104*a*. The lead wire 140*a* is inserted and fixed in a horizontal hole provided in the fixing pin 105*a*. As means for mutually fixing the contact terminal 104*a* and the fixing pin 105*a* to each other, and as means for fixing the fixing pin 105*a* and the lead wire 140*a* to each other, for example, welding, adhesive bonding, connection by pressing the screw, etc., may be employed. The contact terminal 104*a* and the lead wire 140*a* may also be fixed together directly without use of the fixing pin 105*a*. In the same manner, the lead wire 140*b* is fixed to the contact terminal 104*b* through another fixing pin 105*b* (see FIG. 6).

As shown in FIG. 8, the terminal holder 106 is prevented from rotating and is supported in a state enabling displacement in the axial direction (X direction) by the handle frame 15 (see FIG. 3) that is disposed in the interior of the handle 14. In FIG. 8, members on the outer side of the handle frame 15 are omitted from illustration.

When the rotor unit 97 of the slip ring mechanism 96 is rotated accompanying rotation of the drive shaft 66, in the interior of the handle 14, the terminal holder 106 does not rotate except for a certain amount of play between the terminal holder 106 and the handle frame 15. More specifically, although the terminal holder 106 is rotated over a certain amount of backlash thereof between the terminal holder 106 and the handle frame 15, the handle frame 15 functions as a rotation stop, so that the terminal holder 106 does not rotate beyond that amount of backlash. On the other hand, when the rotating axial body 98 is displaced in the axial direction accompanying displacement of the drive shaft 66 in the axial direction in order to perform an opening or closing operation of the gripper 12, the terminal holder 106 and the contact terminals 104a, 104b retained therein are displaced in following relation to the rotating axial body 98.

Figure 9A:
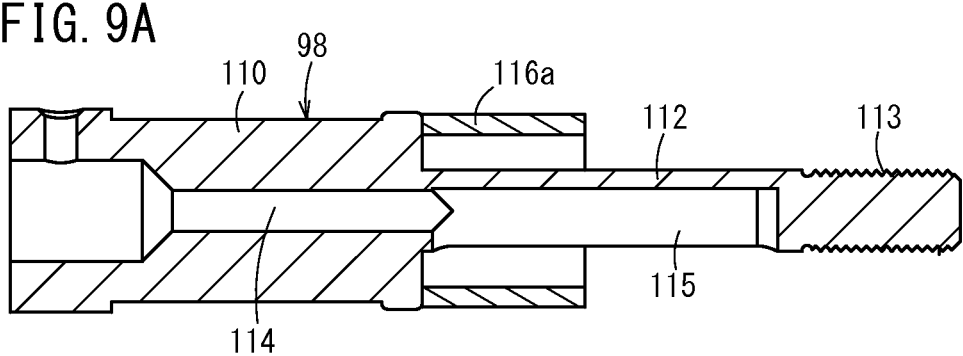
FIG. 9A is a first view for describing an assembly method of the slip ring mechanism.
Figure 9B:
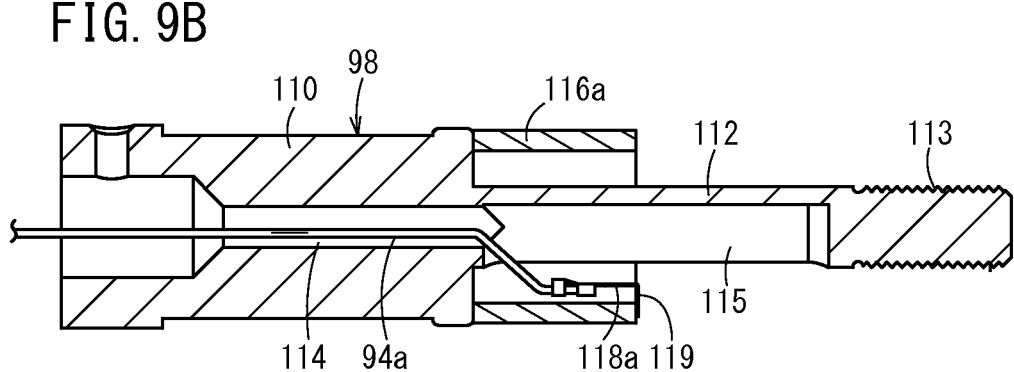
FIG. 9B is a second view for describing the assembly method of the slip ring mechanism.

Next, a method of assembling the slip ring mechanism 96 will be described. As shown in FIG. 9A, the support shaft 112 of the rotating axial body 98 is inserted into a hollow portion of the rotating terminal 116a. Then, as shown in FIG. 9B, the lead wire 94a that is coupled to the conductive member 118a is inserted through the wiring hole 114 via the side hole 115 disposed in the rotating axial body 98, and the conductive member 118a is arranged on the rotating terminal 116a.

Figure 9C:
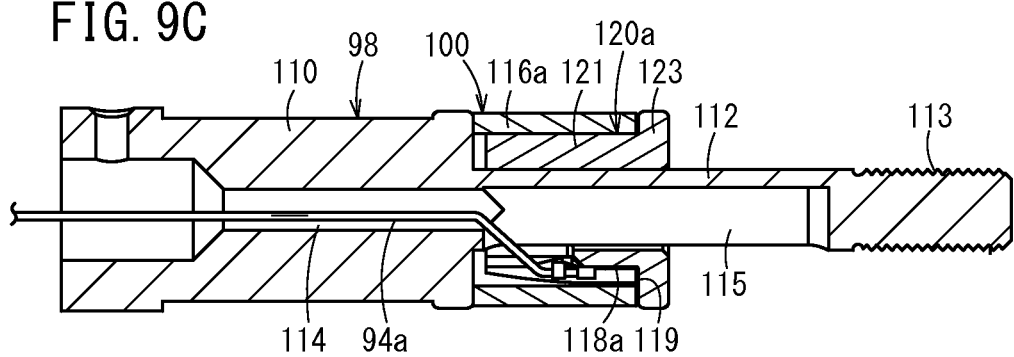
FIG. 9C is a third view for describing the assembly method of the slip ring mechanism.

Next, as shown in FIG. 9C, the retaining member 120a is inserted and fitted into the rotating terminal 116a, whereby the bent end portion 119 of the conductive member 118a is sandwiched between the end surface of the rotating terminal 116a and the flange 123 of the retaining member 120a.

Figure 9D:
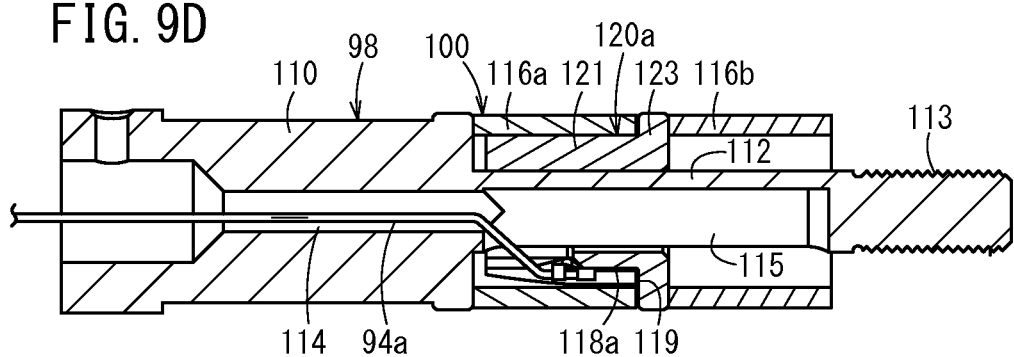
FIG. 9D is a fourth view for describing the assembly method of the slip ring mechanism.
Figure 10A:
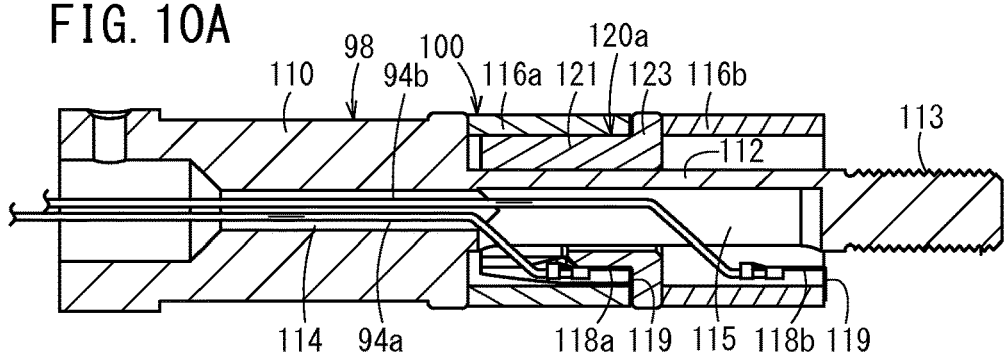
FIG. 10A is a fifth view for describing the assembly method of the slip ring mechanism.

Next, as shown in FIG. 9D, the support shaft 112 of the rotating axial body 98, in a state in which the first ring unit 100 has been assembled, is inserted into the hollow portion of the rotating terminal 116b. Then, as shown in FIG. 10A, the lead wire 94b that is coupled to the conductive member 118b is inserted through the wiring hole 114 via the side hole 115, and the conductive member 118b is arranged on the rotating terminal 116b.

Figure 10B:
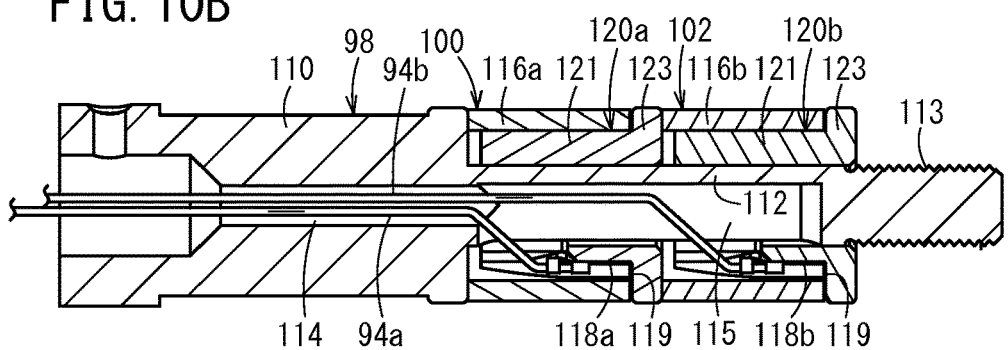
FIG. 10B is a sixth view for describing the assembly method of the slip ring mechanism.

Next, as shown in FIG. 10B, the retaining member 120b is inserted and fitted into the rotating terminal 116b, whereby the bent end portion 119 of the conductive member 118b is sandwiched between the end surface of the rotating terminal 116b and the flange 123 of the retaining member 120b.

Figure 10C:
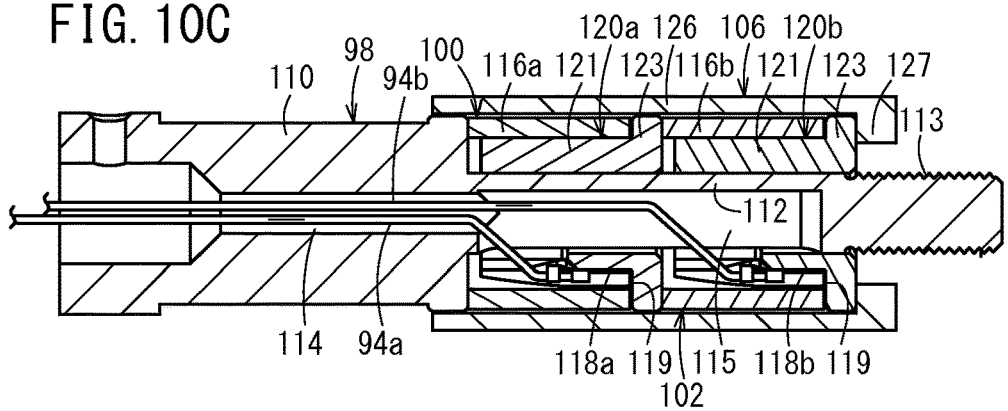
FIG. 10C is a seventh view for describing the assembly method of the slip ring mechanism.

Next, as shown in FIG. 10C, the terminal holder 106 is mounted so that the first ring unit 100 and the second ring unit 102 are covered by the case 126. At this time, by the inwardly projecting portion 127 disposed on the proximal end of the case 126 abutting against the flange 123 of the retaining member 120b, positioning of the terminal holder 106 in the axial direction with respect to the rotating axial body 98 is effected.

Figure 10D:
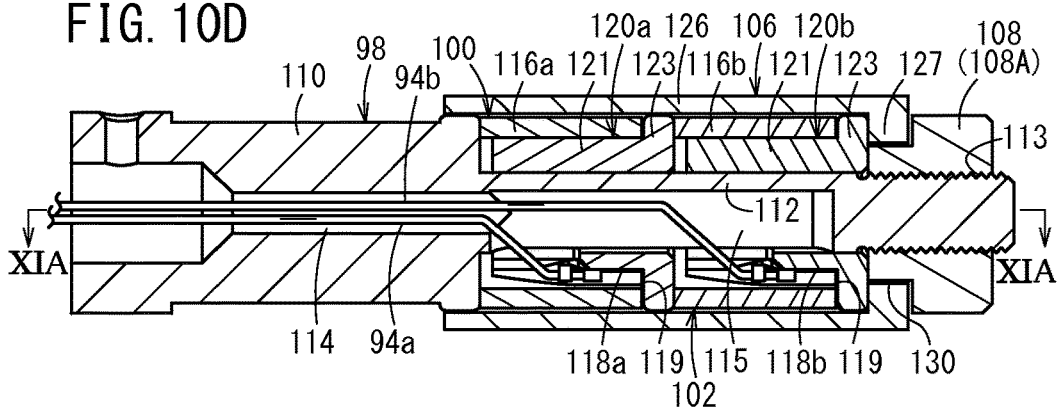
FIG. 10D is an eighth view for describing the assembly method of the slip ring mechanism.
Figure 11A:
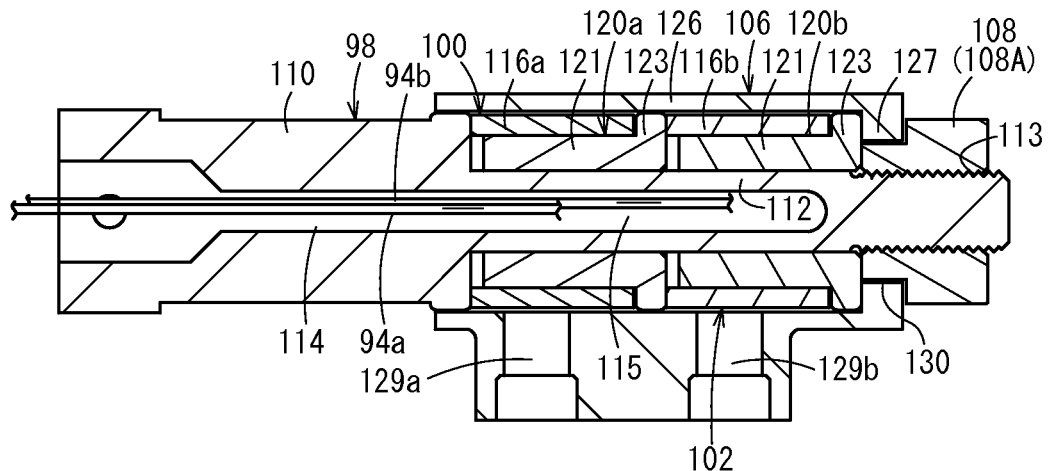
FIG. 11A is a ninth view for describing the assembly method of the slip ring mechanism.

Then, as shown in FIG. 10D, the pressure applying member 108 is fixed with respect to the rotating axial body 98, and the first ring unit 100 and the second ring unit 102 are sandwiched between the rotating axial body 98 and the pressure applying member 108. In the present embodiment, more specifically, the nut 108A is screw-engaged with the male threads 113 disposed on the rotating axial body 98, and is fastened in a fixed state. FIG. 11A is a cross-sectional view taken along line XIA-XIA of FIG. 10D.

Figure 11B:
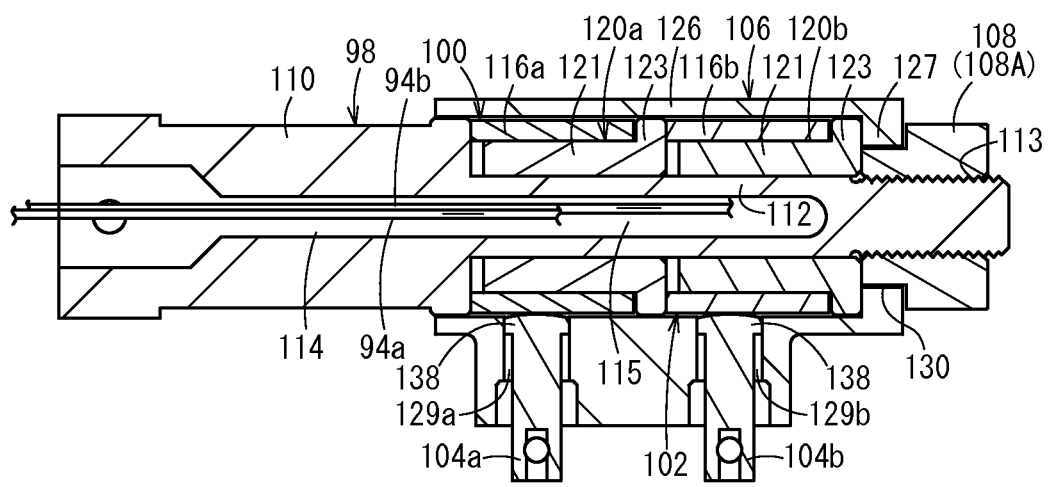
FIG. 11B is a tenth view for describing the assembly method of the slip ring mechanism.

Next, as shown in FIG. 11B, the contact terminals 104a, 104b are inserted respectively from the sides of the head portions 138 thereof into the retaining holes 129a, 129b of the terminal holder 106. Then, as shown in FIG. 6, the biasing members 132a, 132b and the fixing parts 134a, 134b are inserted and fixed respectively in the retaining holes 129a, 129b, resulting in a state in which the contact terminals 104a, 104b are assembled in the terminal holder 106. By carrying out the steps described above, assembly of the slip ring mechanism 96 is completed.

The manipulator 10 according to the present embodiment is constructed basically as described above. Next, operations and advantages of the manipulator 10 will be described.

According to the slip ring mechanism 96, upon rotation of the drive shaft 66, the rotating axial body 98, the first ring unit 100, the second ring unit 102, and the pressure applying member 108 are rotated together in unison. At this time, although the terminal holder 106 and the contact terminals 104a, 104b, which are retained in the terminal holder 106, are not rotated, they are maintained in contact with the outer circumferential surfaces of the rotating terminals 116a, 116b. Consequently, an output from a high frequency power supply device can suitably be supplied through the lead wires 94a, 94b to the gripper 12.

In particular, according to the slip ring mechanism 96 of the present embodiment, the conductive members 118a (118b) are retained in a state of being sandwiched and pressed by the rotating terminals 116a (116b) and the retaining members 120a (120b). Therefore, the slip ring mechanism 96 can easily be assembled without using a bonding means such as soldering, an adhesive, or the like.

Further, due to such a structure, even in the case that a sterilization treatment is applied to the medical manipulator 10 including the slip ring mechanism 96, the electrically conductive state between the conductive members 118a (118b) and the rotating terminals 116a (116b) can suitably be maintained.

The bent end portions 119 of the conductive members 118a (118b) are sandwiched and gripped in the axial direction between the end surfaces of the rotating terminals 116a (116b) and the flanges 123 of the retaining members 120a (120b). Therefore, the electrically conductive state between the conductive members 118a (118b) and the rotating terminals 116b (116b) can suitably be assured.

In the case of the present embodiment, since the slip ring mechanism 96 includes the pressure applying member 108 that applies a load in the axial direction to the rotating terminals 116a (116b), the conductive members 118a (118b), and the retaining members 120a (120b), the electrically conductive state between the conductive members 118a (118b) and the rotating terminals 116a (116b) can more suitably be secured.

In the present embodiment, the pressure applying member 108 is fixed by screw-engagement to the rotating axial body 98. According to this configuration, with a simple structure, the conductive members 118a (118b) can be effectively maintained while being sandwiched and pressed between the rotating terminals 116a (116b) and the retaining members 120a (120b).

In the case of the present embodiment, the terminal holder 106 is capable of rotating relatively with respect to the rotating axial body 98, and is displaceable in the axial direction integrally with the rotating axial body 98. According to this configuration, the terminal holder 106 that retains the contact terminals 104a, 104b also is displaced together therewith accompanying displacement of the rotating axial body 98 in the axial direction. Therefore, when the rotating terminals 116a (116b) are displaced in the axial direction, the positional relationship in the axial direction between the rotating terminals 116a (116b) and the contact terminals 104a (104b) does not change. Consequently, together with displacement of the rotating terminals 116a (116b) in the axial direction, the contact terminals 104a (104b) do not become caught on the rotating terminals 116a (116b).

In the case of the present embodiment, in the slip ring mechanism 96, the first ring unit 100 and the second ring unit 102, in which the rotating terminals 116a, 116b, the conductive members 118a, 118b, and the retaining members 120a, 120b are included respectively, are arranged along an axial direction, and the contact terminals 104a, 104b are provided for the first and second ring units 100, 102, respectively. According to this structure, a medical manipulator 10 that functions as a bipolar type of electrosurgical scalpel can suitably be handled.

In the present embodiment, the terminal holder 106 includes the case 126, in which the first ring unit 100 and the second ring unit 102 are contained in common, and a retaining part 128 that retains the two contact terminals 104a, 104b. According to this configuration, since the first ring unit 100 and the second ring unit 102 are accommodated in the single case 126, the structure can be simplified.

In the present embodiment, in the slip ring mechanism 96, the single terminal holder 106 is provided, in which the first ring unit 100 and the second ring unit 102 are contained in common. However, in a modification of the slip ring mechanism 96, two terminal holders may be provided that separately accommodate the first ring unit 100 and the second ring unit 102.

With the present embodiment, the manipulator 10 is constituted as a bipolar type of electrosurgical scalpel, in which supply of current of different polarities to the first gripper member 12a and the second gripper member 12b is carried out. However, in a modification thereof, the manipulator 10 may be constituted as a monopolar type of electrosurgical scalpel, in which either one of the first gripper member 12a or the second gripper member 12b is electrically energized. In this case, since only one current supply path is needed for supplying power to the gripper 12, a configuration may be provided in which one of the first ring unit 100 (and the contact terminal 104a connected thereto) or the second ring unit 102 (and the contact terminal 104a connected thereto) is eliminated.

Although a certain preferred embodiment of the present invention has been shown and described in detail above, it should be understood that various changes and modifications may be made to the embodiment without departing from the spirit and scope of the invention as set forth in the appended claims.

What is claimed is:

1. A medical manipulator comprising:
   an end effector configured to carry out a rolling operation;
   a drive shaft that transmits at least a rotary driving force to the end effector; and
   a slip ring mechanism that is connected to the drive shaft;
   wherein the slip ring mechanism includes:
      a rotating axial body that rotates together with the drive shaft;
      a rotating terminal arranged coaxially with the rotating axial body;
      a conductive member that contacts the rotating terminal and is electrically connected to the end effector;
      a retaining member that holds the conductive member such that the conductive member is sandwiched between the retaining member and the rotating terminal; and
      two contact terminals that contact the rotating terminal in a condition enabling rotation and sliding relative to the rotating terminal;
   wherein:
      in the slip ring mechanism, a first ring unit and a second ring unit, in each of which the rotating terminal, the conductive member, and the retaining member are included, are arranged along an axial direction of the rotating axial body; and
      the two contact terminals are provided corresponding respectively to the first ring unit and the second ring unit.

2. The medical manipulator according to claim 1, wherein:
   a bent end portion is disposed on the conductive member;
   a flange is disposed on the retaining member; and
   the bent end portion of the conductive member is sandwiched between an end surface of the rotating terminal and the flange.

3. The medical manipulator according to claim 2, wherein the slip ring mechanism includes a pressure applying member that applies a load in the axial direction to the rotating terminal, the conductive member, and the retaining member.

4. The medical manipulator according to claim 3, wherein the pressure applying member is fixed by screw-engagement to the rotating axial body.

5. The medical manipulator according to claim 1, wherein:
   the rotating axial body is displaceable in the axial direction together with the drive shaft;
   the slip ring mechanism includes a terminal holder that retains the contact terminals; and
   the terminal holder is rotatable relative to the rotating axial body, and is displaceable in the axial direction in unison with the rotating axial body.

6. The medical manipulator according to claim 5, wherein:
   the terminal holder includes a case in which the first ring unit and the second ring unit are accommodated in common, and a retaining part that retains the two contact terminals.

7. A medical manipulator comprising:
   an end effector configured to carry out a rolling operation;
   a drive shaft that transmits at least a rotary driving force to the end effector; and
   a slip ring mechanism that is connected to the drive shaft;
   wherein the slip ring mechanism includes:
      a rotating axial body that rotates together with the drive shaft;
      a rotating terminal arranged coaxially with the rotating axial body;
      a conductive member that contacts the rotating terminal and is electrically connected to the end effector;
      a retaining member that holds the conductive member such that the conductive member is sandwiched between the retaining member and the rotating terminal;
      a contact terminal that contacts the rotating terminal in a condition enabling rotation and sliding relative to the rotating terminal;
      a bent end portion is disposed on the conductive member;
      a flange is disposed on the retaining member; and
      the bent end portion of the conductive member being sandwiched between an end surface of the rotating terminal and the flange.

8. The medical manipulator according to claim 7, wherein the slip ring mechanism includes a pressure applying member that applies a load in an axial direction to the rotating terminal, the conductive member, and the retaining member.

9. The medical manipulator according to claim 8, wherein the pressure applying member is fixed by screw-engagement to the rotating axial body.

10. The medical manipulator according to claim 7, wherein:
   the rotating axial body is displaceable in an axial direction together with the drive shaft;
   the slip ring mechanism includes a terminal holder that retains the contact terminal; and
   the terminal holder is rotatable relative to the rotating axial body, and is displaceable in the axial direction in unison with the rotating axial body.

11. The medical manipulator according to claim 10, wherein:
   in the slip ring mechanism, a first ring unit and a second ring unit, in each of which the rotating terminal, the conductive member, and the retaining member are included, are arranged along an axial direction of the rotating axial body;

two contact terminals are provided corresponding respectively to the first ring unit and the second ring unit; and the terminal holder includes a case in which the first ring unit and the second ring unit are accommodated in common, and a retaining part that retains the two contact terminals.

12. A medical manipulator comprising:

an end effector configured to carry out a rolling operation;

a drive shaft that transmits at least a rotary driving force to the end effector; and a slip ring mechanism that is connected to the drive shaft;

wherein the slip ring mechanism includes:

a rotating axial body that rotates together with the drive shaft;

a rotating terminal arranged coaxially with the rotating axial body;

a conductive member that contacts the rotating terminal and is electrically connected to the end effector;

a retaining member that holds the conductive member such that the conductive member is sandwiched between the retaining member and the rotating terminal; and a contact terminal that contacts the rotating terminal in a condition enabling rotation and sliding relative to the rotating terminal;

wherein:

the rotating axial body is displaceable in the axial direction together with the drive shaft;

the slip ring mechanism includes a terminal holder that retains the contact terminal; and the terminal holder is rotatable relative to the rotating axial body, and is displaceable in the axial direction in unison with the rotating axial body.

13. The medical manipulator according to claim 12, wherein:

in the slip ring mechanism, a first ring unit and a second ring unit, in each of which the rotating terminal, the conductive member, and the retaining member are included, are arranged along an axial direction of the rotating axial body;

two contact terminals are provided corresponding respectively to the first ring unit and the second ring unit; and the terminal holder includes a case in which the first ring unit and the second ring unit are accommodated in common, and a retaining part that retains the two contact terminals.

* * * * *